United States Patent [19]
Barnett

[11] 3,937,714

[45] Feb. 10, 1976

[54] EXCHANGE AMINATION PROCESS FOR PREPARING 2-HYDRAZINOBENZOTHIAZOLES

[75] Inventor: Charles J. Barnett, Indianapolis, Ind.

[73] Assignee: Eli Lilly and Company, Indianapolis, Ind.

[22] Filed: Mar. 11, 1974

[21] Appl. No.: 450,024

Related U.S. Application Data

[63] Continuation-in-part of Ser. No. 296,381, Oct. 10, 1972, abandoned.

[52] U.S. Cl. .............................................. 260/305
[51] Int. Cl.$^2$ .................................... C07D 277/82
[58] Field of Search .................................. 260/305

[56] References Cited

OTHER PUBLICATIONS

Solovieva et al., *Chem. Abstracts*, 54:8793, (1960).

*Primary Examiner*—Richard J. Gallagher
*Assistant Examiner*—Anne Marie T. Tighe
*Attorney, Agent, or Firm*—Kathleen R. S. Page; Everet F. Smith

[57] ABSTRACT

Improved process for the preparation of 2-hydrazinobenzothiazoles, comprising the reaction of corresponding 2-aminobenzothiazoles with hydrazine in the presence of acid, preferably in a selected solvent.

26 Claims, No Drawings

EXCHANGE AMINATION PROCESS FOR PREPARING 2-HYDRAZINOBENZOTHIAZOLES

CROSS-REFERENCE TO RELATED APPLICATION

This is a continuation-in-part of my copending application Ser. No. 296,381, filed Oct. 10, 1972 and abandoned after the filing of the present application.

BRIEF SUMMARY OF THE INVENTION

The term "exchange amination" is used to refer to the exchange of one amino group for another, including the exchange of a hydrazino group for an amino group. See Houben-Weyl, Methoden Der Organischen Chemie, Band 10/2, 278 (Georg Thieme Verlag, Stuttgart, 1967); Ann. 686, 134 (1965); J. Amer. Chem. Soc. 74, 1648 (1952); J. Amer. Chem. Soc. 82, 3971 (1960); and J. Gen. Chem. U.S.S.R. (eng. trans.) 29, 2036 (1959).

The last-named of these references reports the preparation and attempted preparation of numerous 2-hydrazinobenzothiazoles by reaction of hydrazine with 2-aminobenzothiazole and various ring-substituted 2-aminobenzothiazoles. However, the results were less than entirely satisfactory. Some of the reactions yielded no hydrazinobenzothiazole product. Unsubstituted 2-aminobenzothiazole gave the desired product, but accompanied by a substantial amount of o-aminothiophenol, formed by ring opening and isolated as the disulfide. Only carboxy-substituted aminobenzothiazoles gave good yields.

The present invention is in a process for the preparation of a compound of the formula:

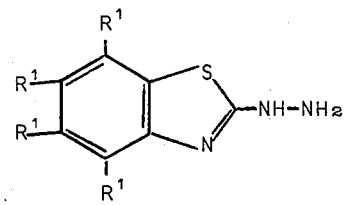

wherein each $R^1$ independently represents hydrogen, halo, lower alkyl of $C_1$-$C_3$, lower alkoxy of $C_1$-$C_3$, or lower alkylthio of $C_1$-$C_3$, subject to the limitation that at least two $R^1$'s represent hydrogen; which process comprises reacting a corresponding 2-aminobenzothiazole compound of the formula:

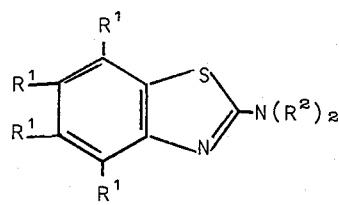

wherein each $R^2$ independently represents hydrogen or methyl with hydrazine in the presence of at least a catalytic amount of acid. "Halo" is employed in the present specification and claims to designate bromo, chloro, and fluoro.

The resulting 2-hydrazinobenzothiazole products are useful as starting materials for the preparation of s-triazolo (3,4-b) benzothiazole compounds of the formula:

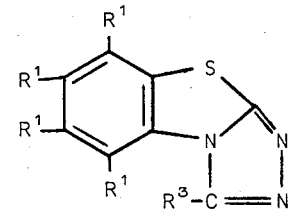

wherein $R^3$ is, inter alia, hydrogen or any of a number of other moieties. These compounds are useful as agents for the control of plant-pathogenic organisms.

DETAILED DESCRIPTION OF THE INVENTION

The use of acid is essential to the present invention, but its identity is not. A wide variety of acidic substances has proven useful in the present invention, including phenol; organic acids, such as acetic acid, benzoic acid, formic acid, malonic acid, oxalic acid, p-toluenesulfonic acid, phenylacetic acid, and citric acid; and mineral acids such as hydrochloric acid, hydrobromic acid, and sulfuric acid.

Although the Arrhenius definition of acid as a substance which dissociates in water into hydrogen ions (protons) and anions has been supplemented by more sophisticated definitions, this concept of acid is useful in the context of the present invention. It is believed that the acid functions both as a catalyst and as a reagent which, with hydrazine, forms hydrazinium ion; and that the presence of some hydrazinium ion favors the desired reaction, although the precise mechanism is not understood. Therefore, any substance which, under the reaction conditions described, undergoes a protolytic reaction with hydrazine--consistent with the Arrhenius definition--is workable in the present invention.

In practice, however, stronger acids, such as those exhibiting a $pK_a$ of 5 or less, function more effectively. It is most convenient to use a mineral acid, such as hydrochloric acid, hydrobromic acid, or sulfuric acid. Particularly preferred mineral acids are hydrochloric acid and hydrobromic acid.

The acid can be supplied to the reaction mixture in any of a variety of ways. It can be added separately or it can be supplied as a salt of either the 2-aminobenzothiazole compound or the hydrazine.

The quantity of acid supplied is not critical; a small catalytic amount improves the yield of product substantially over that obtained when no acid is used at all. However, somewhat larger amounts are not deleterious. In general, the present process goes forward when employing acid in the ratio of 0.1 to 1.0 molecular proportion of acid for each molecular proportion of hydrazine. A preferred ratio is from 0.33 to 0.5 molecular proportion of acid for every molecular proportion of hydrazine.

While the prior art has often used excess hydrazine to serve in part as solvent, it has been found that the use of a solvent inert to the reaction is preferable. The solvent should be one which is miscible with hydrazine and which, in combination with the reagents, refluxes at a temperature of at least about 100°C., and preferably at higher temperatures such as 120°-150°C. Preferred solvents include $C_2$-$C_4$-alkylenediols, such as ethylene glycol, propylene glycol, 1,4-butanediol, and 2,3-butanediol; di- and tri(ethylene and propylene) glycols, including diethylene glycol, triethylene glycol, dipropylene glycol, and tripropylene glycol; mono($C_1$-$C_4$-alkyl) ethers of ethylene and propylene glycols, such as ethylene glycol monomethyl ether, ethylene glycol monoethyl ether, ethylene glycol mono-n-butyl ether, and propylene glycol monomethyl ether; mono($C_1$-$C_4$-alkyl) ethers of di- and tri(ethylene and propylene) glycols, such as diethylene glycol monomethyl ether, diethylene glycol monoethyl ether, and diethylene glycol mono-n-butyl ether; triethanolamine; sulfolane; and dimethylsulfoxide. As used herein, the term "$C_2$-$C_4$-alkylenediols" refers only to non-gem diols. Although water is not a preferred solvent, minor amounts of it are not deleterious to the reaction. Therefore, it is acceptable to supply the hydrazine as any of the various commercially-available forms which include water.

It is not critical that the 2-aminobenzothiazole and the hydrazine by employed in any specific ratio to one another. The prior art has often employed a large excess of hydrazine. However, it has now been found that, in the instance of some of the 2-aminobenzothiazole compounds, formation of side products is enhanced by higher hydrazine concentrations. Also, since the reaction consumes the reactants in only equimolecular amounts, the use of excess hydrazine is inefficient. Good results in the practice of the present invention have been achieved with from one to not more than about ten molecular proportions of hydrazine per molecular proportion of the 2-aminobenzothiazole. Better results are obtained with from about three to about five molecular proportions of hydrazine per molecular proportion of the 2-aminobenzothiazole.

The temperature at which the reaction is conducted is not critical. In general, the reaction goes forward at temperatures of 100°C. and higher. Typically, temperatures of 100°–150°C. have been found to give good results; better results are generally obtained at temperatures of 120°–150°C.

Typically, the desired product precipitates in the reaction mixture and is separated by filtration. However, other conventional separation procedures can be employed. Product produced by the present process is generally of high purity, in some instances as high as 98 percent; but when desired, the separated product can be purified by conventional procedures.

The following examples illustrate the present invention and will enable those skilled in the art to practice the same.

EXAMPLE 1:

2-HYDRAZINOBENZOTHIAZOLE

To a slurry of 30 g. (0.2 mole) 2-aminobenzothiazole in 150 ml. ethylene glycol was added 23.7 g. (0.4 mole) 85% hydrazine hydrate and 13.7 g. (0.2 mole) hydrazine monohydrochloride. The mixture was stirred under a nitrogen atmosphere and heated at a temperature of 140°C. for 2 hours. The product crystallized on cooling. After addition of 50 ml. water and stirring, the material was filtered, washed with 100 ml. water in three portions, and dried in vacuo at 60°C. There was obtained 29.9 g. (90.6% of theory) 2-hydrazinobenzothiazole, m.p. 194°–198°, assay (titration) 97.0%. Recrystallization from ethanol gave 20 g., m.p. 198°–199°C. [Lit. m.p. 199°–200°C., I. A. Solov'eva and A. G. Guseva, J. Gen. Chem. U.S.S.R. 29, 2036 (1959)]. An additional 4 g., m.p. 196.5°–198.5°C., was obtained from the second crop.

EXAMPLE 2:

5,6-DIMETHYL-2-HYDRAZINOBENZOTHIAZOLE 5,6-Dimethyl-2-aminobenzothiazole (5.0 g., 0.028 mole), 85% hydrazine hydrate (3.49 g.; 0.056 mole) and hydrazine monohydrochloride (1.99 g.; 0.028 mole) were reacted in the procedures of Example 1. 5,6-Dimethyl-2-hydrazinobenzothiazole was obtained in 82% yield, m.p. 223°–228°C. Assay (titration) 97.2%. Recrystallization from ethanol gave material melting 235°–237°C. (dec.).

Anal. Calc'd. for $C_9H_{11}N_3S$: C, 55.93; H, 5.74; N, 21.74; S, 16.59. Found: C, 55.96; H, 5.78; N, 21.55; S, 16.72.

EXAMPLE 3:

4-CHLORO-2-HYDRAZINOBENZOTHIAZOLE

4-Chloro-2-aminobenzothiazole (10.09 g.; 0.0543 mole), 85% hydrazine hydrate (6.45 g.; 0.109 mole), and hydrazine monohydrochloride (3.72 g.; 0.109 mole) were reacted in the procedures of Example 1. There was obtained 9.77 g. (90% of theory) 4-chloro-2-hydrazinobenzothiazole, m.p. 226°–229°C.; assay (titration) 96.2%. Recrystallization from isopropanol gave 7.2 g., m.p. 239°–241°C.

Anal. Calc'd. for $C_7H_6N_3ClS$: C, 42.11; H, 3.03; N, 21.05; S, 16.06; Cl, 17.76. Found: C, 42.07; H, 2.94; N, 20.82; S, 16.11; Cl, 17.81.

EXAMPLE 4:

4-METHOXY-2-HYDRAZINOBENZOTHIAZOLE

4-Methoxy-2-aminobenzothiazole (5.0 g.; 0.028 mole), 85% hydrazine hydrate (3.3 g.; 0.057 mole), and hydrazine monohydrochloride (1.9 g.; 0.028 mole) were reacted in the procedures of Example 1. There was obtained 4.85 g. 4-methoxy-2-hydrazinobenzothiazole, m.p. 215°–220°C., assay (titration) 97.1%. The analytical sample had m.p. 224°–226.5°C. (from methanol).

Anal. Calc'd. for $C_8H_9N_3OS$: C, 49.21; H, 4.65; N, 21.52; S, 16.42. Found: C, 49.25; H, 4.54; N, 21.67; S, 16.40.

EXAMPLE 5:

4-METHYL-2-HYDRAZINOBENZOTHIAZOLE

A mixture of 11.95 g. (0.049 mole) 4-methyl-2-aminobenzothiazole hydrobromide and 8.60 g. (0.15 mole), 85% hydrazine hydrate in 40 ml. ethylene glycol was heated under nitrogen at a temperature of 140°C. for 2 hours. The mixture was cooled to room temperature and 40 ml. water added. The product, which began to precipitate during the cooling period, was filtered, washed with water, and dried in vacuo at 60°C. There was obtained 8.30 g. (93% of theoretical) 4-methyl-2-hydrazinobenzothiazole, m.p. 165°–168°C. Thin layer chromatography of the crude product showed that it was free of starting material and substantially pure. The analytical sample had m.p. 167°–169°C. (from ethanol).

Anal. Calc'd. for $C_8H_9N_3S$: C, 53.61; H, 5.06; N, 23.44; S, 17.89. Found: C, 53.84; H, 4.98; N, 23.44; S, 17.68.

EXAMPLE 6:

6-METHOXY-2-HYDRAZINOBENZOTHIAZOLE

6-Methoxy-2-aminobenzothiazole (2.70 g.; 0.015 mole), 85% hydrazine hydrate (1.77 g.; 0.03 mole), and hydrazine monohydrochloride (1.03 g.; 0.015 mole) were reacted in the procedures of Example 1, yielding 2.63 g. (90% of theory) 6-methoxy-2-hydrazinobenzothiazole, m.p. 172°–175°C. Assay (titration) 97.0% (Lit. m.p. 168°–169°C. O. Bayer, E. Herdieckerhoff, and H. Schindhelm, (to I. G. Farbenind. A. G.) U.S. Pat. No. 2,073,600, Mar. 16, 1937).

2,073,600, Mar. 16, 1937).

EXAMPLE 7:

6-METHYLTHIO-2-HYDRAZINOBENZOTHIAZOLE

6-Methylthio-2-aminobenzothiazole (10.0 g.; 0.05 mole), 85% hydrazine hydrate (6.50 g.; 0.10 mole), and hydrazine monohydrochloride (3.5 g.; 0.05 mole) were reacted in the procedures of Example 1, yielding 9.95 g. (92.5% of theory) 6-methylthio-2-hydrazinobenzothiazole, m.p. 173°–176°C. Assay (titration) 98.0%. The analytical sample melted 178°–180°C. (from ethanol).

Anal. Calc'd. for $C_8H_9N_3S_2$:

C, 45.47; H, 4.29; N, 19.89; S, 30.30. Found: C, 45.69; H, 4.30; N, 19.67; S, 30.63.

EXAMPLES 8–14:

Numerous reactions of 4-methyl-2-aminobenzothiazole hydrobromide with hydrazine hydrate were conducted in accordance with the present invention, varying the solvent. The solvents employed, with reaction times, reaction temperatures, and yields of products were as follows:

| Solvent | Reaction Period | Reaction Temperature | Yield of Product |
| --- | --- | --- | --- |
| diethylene glycol | 80 minutes | 140°C. | 91% |
| propylene glycol | 2 hours | 140°C. | 93% |
| 2,3-butanediol | 3 hours | 125°C. | 88% |
| triethanolamine | 3 hours | 134–140°C. | 91% |
| sulfolane | 5½ hours | 129°C. | 85% |
| DMSO | 4 hours | 125°C. | >95% |
| ethylene glycol monomethyl ether | 5½ hours | 110°C. | 85% |

EXAMPLE 15:

4-METHYL-2-HYDRAZINOBENZOTHIAZOLE

4-Methyl-2-dimethylaminobenzothiazole hydrobromide (10.95 g.; 0.04 mole), 85% hydrazine hydrate representing 8.01 g., 0.12 mole, and 33 ml. of ethylene glycol were mixed at room temperature and the mixture heated to 140°C. under nitrogen atmosphere. The reaction mixture was maintained at this temperature overnight. After 39 hours of reaction time, the reaction was cooled, diluted with 33 ml. of water, and filtered to separate the desired 4-methyl-2-hydrazinobenzothiazole compound. It was washed with water and dried 2 hours at 65°C. in vacuo, 5.43 g., 79% yield. The product was subjected to nmr, which showed about 5–10% of starting material. The melting point was 161°–166°C.

EXAMPLE 16:

4-METHYL-2-HYDRAZINOBENZOTHIAZOLE

4-Methyl-2-aminobenzothiazole (8.21 g.; 0.05 mole), hydrazine monohydrochloride (1.14 g.; 0.017 mole), 85% hydrazine hydrate (1.96 g.; 0.033 mole), and 41 ml. of ethylene glycol were mixed, and the mixture heated under $N_2$ atmosphere to 140°C. These reaction conditions were continued for 15 hours; the reaction mixture was then permitted to cool slowly to romm temperature and, for convenience only, stored overnight under $N_2$ atmosphere. Water (45 ml.) was added to the reaction mixture in the morning to force crystallization. The reaction mixture was then filtered to separate the desired 4-methyl-2-hydrazinobenzothiazole compound. It was dried in vacuo overnight at 60°C. The yield was 8.00 g., 89% yield, m.p. 143°–51°C. Non-aqueous titration showed the product to be 85.8% pure.

EXAMPLE 17:

4-CHLORO-2-HYDRAZINOBENZOTHIAZOLE

4-Chloro-2-aminobenzothiazole (2.0 g.; 0.0108 mole) was dissolved in 10 milliliters of diethylene glycol monomethyl ether and 0.9 milliliter of concentrated HC1 added with stirring. 85% Hydrazine hydrate (1.92 g.) was then added to the mixture, and the reaction mixture was heated to 110°C., under $N_2$ atmosphere, on an oil bath. The reaction was continued for 22 hours, the final reaction temperature being 120°C. The 4-chloro-2-hydrazinobenzothiazole product was isolated by addition of water and separated by filtration, 1.69 g. (78% yield), m.p. 232°–235°C.

EXAMPLE 18:

4-METHYL-2-HYDRAZINOBENZOTHIAZOLE

To a suspension of 4-methyl-2-aminobenzothiazole (5.0 g., 0.03 mole) in 20 ml. of ethylene glycol was added 5.4 g. of 85% hydrazine hydrate (0.09 mole) and 2.75 g. (0.046 mole) acetic acid. The mixture was heated to 126°C. under $N_2$ atmosphere for 3 hours. On cooling and dilution with about ½ volume of water the product crystallized. There was obtained 4.73 g. (87% of theory) 4-methyl-2-hydrazinobenzothiazole. The product was identified by thin layer chromatography and found to be substantially pure.

EXAMPLE 19:

4-METHYL-2-HYDRAZINOBENZOTHIAZOLE

4-Methyl-2-methylaminobenzothiazole hydrobromide (443 g.; 1.71 mole) was added with stirring to 1.7 liter of ethylene glycol. 85% Hydrazine hydrate (400 grams; 6.75 mole) was added in several portions. The reaction mixture was heated to 130°–135°C. under $N_2$ atmosphere and maintained for about four hours, then cooled slowly with stirring. The product was isolated by addition of water and separated by filtration. It was then dried overnight in a vacuum oven, yielding 275.5 g. (90% yield) of 4-methyl-2-hydrazinobenzothiazole. The nmr spectrum agreed with a reference spectrum and showed no evidence of starting material or other impurity. Non-aqueous titration showed the product to be 97.5% pure.

The products of the present process:

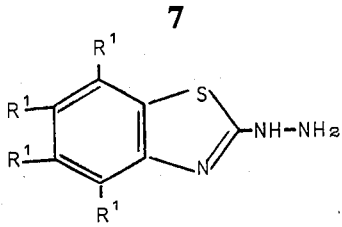

are useful as starting materials for the preparation of s-triazolo (3,4-b) benzothiazole compounds of the formula:

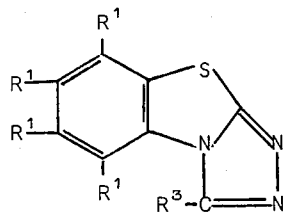

wherein $R^3$ is, inter alia, hydrogen or lower alkyl such as methyl. The conversion of the 2-hydrazinobenzothiazoles to the s-triazolo (3,4-b) benzothiazoles can be accomplished in any of several procedures. In one procedure, the 2-hydrazinobenzothiazole is converted directly by reaction with an ortho ester ($R^3$-C(O-alkyl)$_3$); in another procedure, the 2-hydrazinobenzothiazole is acylated and the resulting 2-(2-acylhydrazino) benzothiazole cyclized by refluxing with phenol. In a third procedure, the 2-hydrazinobenzothiazole is likewise converted directly by reaction with an acid ($R^3$COOH).

By any synthetic route, the s-triazolo (3,4-b) benzothiazole products are useful as agents for the control of plant pathogenic organisms, especially fungal organisms and particularly the causative organism of rice blast (*Piricularia oryzae*). In employing these products for such control, the products are effective when applied by any of a variety of routes: to the foliage of plants to be protected, to seeds, to the surface of soil or water in which are growing the plants to be treated, as a transplant root soak, etc. The products are more conveniently applied if formulated with conventional adjuvants such as surfactants, etc. The amount of compound which is effective is not critical and depends in part upon the route of application and the organism sought to be controlled. Representative rates at which good control of rice blast is obtained are as follows: in liquid formulations suited for seed treatment, transplant root soak, or spray application to foliage, from about 0.001 to 0.2 percent by weight; and in acreage application, such as for surface application, from 0.5 to 2.0 or more pounds per acre.

The compounds to be employed as starting materials in the process of the present invention:

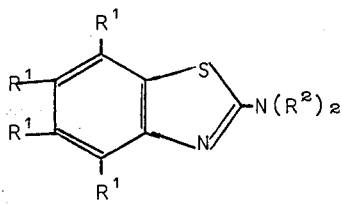

are available compounds. Many are commercially available. All can be synthesized by known synthetic procedures. A convenient method is the Hugerschoff reaction: see Heterocyclic Compounds, Vol. 5, ed. by Elderfield (John Wiley & Sons, Inc., New York, 1957), page 506.

I claim:

1. Process for the preparation of a compound of the formula

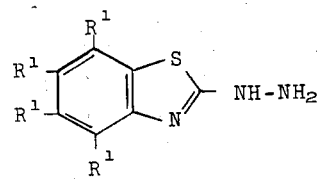

wherein each $R^1$ independently represents hydrogen, halo, lower alkyl of $C_1$-$C_3$, lower alkoxy of $C_1$-$C_3$, or lower alkylthio of $C_1$-$C_3$, subject to the limitation that at least two $R^1$'s represent hydrogen; which process comprises reacting a corresponding 2-aminobenzothiazole compound of the formula

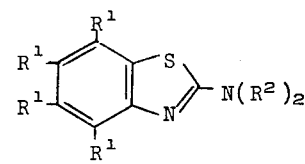

wherein each $R^2$ independently represents hydrogen or methyl with hydrazine in the presence of at least a catalytic amount of an acid exhibiting a $pK_a$ of 5 or less, at a temperature above 100°C., and in a solvent selected from the group consisting of $C_2$-$C_4$-alkylenediols; di- and tri(ethylene and propylene) glycols; mono($C_1$-$C_4$-alkyl) ethers of ethylene and propylene gylcols; mono($C_1$-$C_4$-alkyl) ethers of di- and tri(ethylene and propylene) glycols; triethanolamine; sulfolane; and dimethylsulfoxide.

2. The process of claim 1 wherein the 2-aminobenzothiazole compound is 2-aminobenzothiazole.

3. The process of claim 1 wherein the 2-aminobenzothiazole compound is 4-methyl-2-aminobenzothiazole.

4. The process of claim 1 wherein the 2-aminobenzothiazole compound is 4-chloro-2-aminobenzothiazole.

5. The process of claim 1 wherein the solvent is propylene glycol.

6. The process of claim 5 wherein the 2-aminobenzothiazole compound is 4-methyl-2-aminobenzothiazole.

7. The process of claim 5 wherein the 2-aminobenzothiazole compound is 4-chloro-2-aminobenzothiazole.

8. The process of claim 1 wherein the solvent is ethylene glycol.

9. The process of claim 1 wherein the acid is a mineral acid.

10. The process of claim 9 wherein the solvent is propylene glycol.

11. The process of claim 10 wherein the 2-aminobenzothiazole compound is 4-methyl-2-aminobenzothiazole.

12. The process of claim 10 wherein the 2-aminobenzothiazole compound is 4-chloro-2-aminobenzothiazole.

13. The process of claim 9 wherein the acid is hydrochloric acid, hydrobromic acid, or sulfuric acid.

14. The process of claim 13 wherein the acid is hydrochloric acid.

15. The process of claim 8 wherein the 2-aminobenzothiazole compound is 2-aminobenzothiazole.

16. The process of claim 8 wherein the 2aminobenzothiazole compound is 4-methyl-2-aminobenzothiazole.

17. The process of claim 8 wherein the 2-aminobenzothiazole compound is 4-chloro-2-aminobenzothiazole.

18. Process for the preparation of a compound of the formula

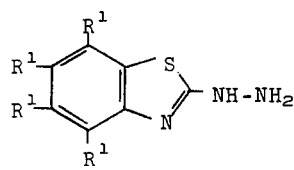

wherein each $R^1$ independently represents hydrogen, halo, lower alkyl of $C_1$-$C_3$, lower alkoxy of $C_1$-$C_3$, or lower alkylthio of $C_1$-$C_3$, subject to the limitation that at least two $R^1$'s represent hydrogen; which process comprises reacting a corresponding 2-aminobenzothiazole compound of the formula

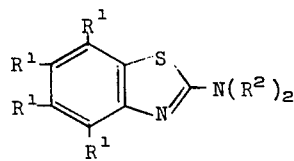

wherein each $R^2$ independently represents hydrogen or methyl with hydrazine under the following conditions:

1. in the presence of an acid exhibiting a $pK_a$ of 5 or less, in the ratio of 0.1 to 1.0 molecular proportion of said acid for each molecular proportion of hydrazine;
2. at a temperature above 100°C.; and
3. in a solvent selected from the group consisting of $C_2$-$C_4$-alkylenediols; di- and tri(ethylene and propylene) glycols; mono($C_1$-$C_4$-alkyl) ethers of ethylene and propylene glycols; mono($C_1$-$C_4$-alkyl) ethers of di- and tri(ethylene and propylene) glycols; triethanolamine; sulfolane; and dimethylsulfoxide.

19. The process of claim 18 wherein the solvent is propylene glycol.

20. The process of claim 19 wherein the 2-aminobenzothiazole compound is 2-aminobenzothiazole.

21. The process of claim 19 wherein the 2-aminobenzothiazole compound is 4-methyl-2-aminobenzothiazole.

22. The process of claim 19 wherein the 2-aminobenzothiazole compound is 4-chloro-2-aminobenzothiazole.

23. The process of claim 18 wherein the solvent is ethylene glycol.

24. The process claim 23 wherein the 2-aminobenzothiazole compound is 2-aminobenzothiazole.

25. The process of claim 23 wherein the 2-aminobenzothiazole compound is 4-methyl-2-aminobenzothiazole.

26. The process of claim 23 wherein the 2-aminobenzothiazole compound is 4-chloro-2-aminobenzothiazole.

* * * * *